(12) United States Patent
Lee et al.

(10) Patent No.: US 10,495,443 B1
(45) Date of Patent: Dec. 3, 2019

(54) FIDUCIAL MARKING SYSTEM

(71) Applicant: Qiagen Sciences, LLC, Germantown, MD (US)

(72) Inventors: Hsu-Yi Lee, Germantown, MD (US); Michel Georges Perbost, Belmont, MA (US)

(73) Assignee: Qiagen Sciences, LLC, Germantown, MD (US)

( * ) Notice: Subject to any disclaimer, the term of this patent is extended or adjusted under 35 U.S.C. 154(b) by 0 days.

(21) Appl. No.: 16/046,446

(22) Filed: Jul. 26, 2018

(51) Int. Cl.
*G01B 11/00* (2006.01)

(52) U.S. Cl.
CPC .................................. *G01B 11/002* (2013.01)

(58) Field of Classification Search
CPC .................................................... G01B 11/002
USPC .......................................................... 235/494
See application file for complete search history.

(56) References Cited

U.S. PATENT DOCUMENTS

| | | | |
|---|---|---|---|
| 2002/0020750 A1* | 2/2002 | Dymetman | G06F 3/03545 235/472.01 |
| 2009/0271753 A1* | 10/2009 | Quandt | G06F 17/5068 716/119 |
| 2014/0034719 A1* | 2/2014 | Summers | G06Q 30/0241 235/375 |
| 2015/0125053 A1 | 5/2015 | Vieceli et al. | |

FOREIGN PATENT DOCUMENTS

WO    2013184796 A1    12/2013

OTHER PUBLICATIONS

International Search Report for International Application No. PCT/US2019/043404, dated Sep. 9, 2019, 8 pages.

* cited by examiner

*Primary Examiner* — Daniel A Hess
(74) *Attorney, Agent, or Firm* — RatnerPrestia

(57) ABSTRACT

Fiducial marking systems provided for forming a global coordinate system for a visual system having a limited field of view. The fiducial marking system includes a target surface that is movable relative to the visual system and a visual pattern associated with the target surface. The visual pattern includes a plurality of first lines and a plurality of second lines. Each first line is spaced by a first distance from each adjacent first line and each second line is spaced by a second distance from each adjacent second line, wherein the first distance is different than the second distance. Additionally, the first distance and the second distance are selected such that at least one first line and at least one second line are within the field of view at all relative positions of the visual system and the target surface.

14 Claims, 9 Drawing Sheets

FIDUCIAL MARKING SYSTEM

FIELD OF THE INVENTION

The present invention relates generally to fiducial marking systems for sequencing instruments or other microscopic devices, and, more particularly, to global coordinate systems formed by fiducial marking systems.

BACKGROUND OF THE INVENTION

Over the past decades, the amount of DNA sequence information generated and deposited into Genbank has grown exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. Other next-generation sequencing technologies may use native nucleotides and/or polymerases or labeled oligonucleotides and ligation enzymes to determine nucleic acid sequences. To attain high throughput, many millions of such template spots, each being either single or multiple cloned molecules, are arrayed across a sequencing chip and their sequence is independently read out and recorded.

Sequencing-by-synthesis instruments often use an optical system, such as a microscope, to detect the nucleobase extensions; although non-optical systems are also known. A typical optical instrument uses visible chemical labels to determine the identity of each extended base pair. A typical problem with such systems is that it can be difficult to reliably track the sequencing progress of individual template spots. This is because the template spots are very small, making optical tracking of their positions difficult and sometimes unreliable. A further problem arises when the optical system or sequencing chip are moved during the course of sequencing. In this situation, it is necessary to re-register the chip with the optical system so that the positions of the individual template spots can be re-established after such movement.

The inventors recognized that there is a need for improved fiducial markers, which may be used as a point of reference for ascertaining a measurement of the location of an item, such as a chemical label.

SUMMARY OF THE INVENTION

Exemplary aspects of the invention are directed generally to fiducial marking systems and to global coordinate systems formed by fiducial marking systems.

In one exemplary aspect, a fiducial marking system is provided for forming a coordinate system for a visual system having a limited field of view. The fiducial marking system includes a target surface that is movable relative to the visual system and a visual pattern associated with the target surface. The visual pattern includes a plurality of first lines and a plurality of second lines. Each first line is spaced by a first distance from each adjacent first line and each second line is spaced by a second distance from each adjacent second line, wherein the first distance is different than the second distance. Additionally, the first distance and the second distance are selected such that at least one first line and at least one second line are within the field of view at all relative positions of the visual system and the target surface.

In another exemplary aspect, a fiducial marking system includes each first line being parallel to each other first line, and the first lines all extending in a first direction.

In another embodiment, a fiducial marking system includes each second line being parallel to each other second line, and the second lines all extending in a second direction.

In a further embodiment, a fiducial marking system includes the first direction being parallel to the second direction.

In yet another embodiment, a fiducial marking system includes the first direction not being parallel to the second direction.

In yet a further embodiment, the fiducial marking system above includes the first direction being angled at 60 degrees relative to the second direction.

In yet another embodiment, a fiducial marking system includes no more than one second line positioned between each adjacent pair of first lines.

In yet a further embodiment, a fiducial marking system includes each second line positioned relative to a respective adjacent pair of first lines in a position that is different from the position of each other second line relative to its respective adjacent pair of first lines.

In yet another embodiment, a fiducial marking system includes the first lines having a first defining visual appearance and the second lines having a second defining visual appearance, and the second defining visual appearance being different from the first defining visual appearance.

In yet a further embodiment, a fiducial marking system includes the first defining visual appearance comprises a first thickness, and the second defining visual appearance comprises a second thickness, the second thickness being different from the first thickness.

In yet another embodiment, a fiducial marking system includes a plurality of third lines, each third line spaced by a third distance from each adjacent third line; and a plurality of fourth lines, each fourth line spaced by a fourth distance from each adjacent fourth line; wherein the third distance is different than the fourth distance; and wherein the third distance and the fourth distance are selected such that at least one third line and at least one fourth line are within the field of view at all relative positions of the visual system and the target surface.

In yet a further embodiment, a fiducial marking system includes the first lines all extending in a first direction; the second lines all extending in a second direction; the third lines all extending in a third direction, the third direction being different than the first direction; and the fourth lines all extending in a fourth direction, the fourth direction being different than the second direction.

In yet another embodiment, a fiducial marking system includes the second direction being parallel with the first direction.

In yet a further embodiment, a fiducial marking system includes the third direction being parallel with the fourth direction.

In yet another embodiment, a fiducial marking system includes the second direction being perpendicular with the first direction, and the fourth direction being perpendicular with the second direction.

In yet a further embodiment, a fiducial marking system includes the second direction being oriented at 60 degrees to the first direction, and the fourth direction being oriented at 60 degrees to the second direction.

In yet another embodiment, a fiducial marking system includes the first lines and the third lines having a first defining visual appearance and the second lines and the fourth lines have a second defining visual appearance, and the second defining visual appearance being different from the first defining visual appearance.

In yet a further embodiment, a fiducial marking system includes the first defining visual appearance comprising a first thickness, and the second defining visual appearance comprising a second thickness, the second thickness being different from the first thickness.

In yet another embodiment, a fiducial marking system includes the first lines intersecting the third lines to form a pattern of first crosshair marks; the second lines intersecting the fourth lines to form a pattern of second crosshair marks; and each of the first crosshair marks and each of the second crosshair marks identifying a unique coordinate location on the target surface.

In yet a further embodiment, a fiducial marking system includes the first lines, the second lines, the third lines and the fourth lines comprising broken lines having a gap between each intersection with each other line, such that each first crosshair mark and each second crosshair mark is separate from each other first crosshair mark and each other second crosshair mark.

In yet another embodiment, a fiducial marking system includes the first lines, the second lines, the third lines and the fourth lines comprising continuous lines, such that each first crosshair mark and each second crosshair mark is connected to each adjacent first crosshair mark and each adjacent second crosshair mark to form a continuous grid pattern on the target surface.

In another exemplary aspect, a fiducial marking system is provided for forming a global coordinate system. The fiducial marking system includes a first grid and a second grid. The first grid is formed by a plurality of first lines and by a plurality of second lines. The plurality of first lines of the first grid extending in a first direction and having a distance between adjacent first lines. The plurality of second lines of the first grid extending in a second direction that is traverse to the first direction and having a distance between adjacent second lines. The second grid is formed by a plurality of first lines and by a plurality of second lines. The plurality of first lines of the second grid extend in a first direction and have a distance between adjacent first lines. The plurality of second lines of the first grid have a distance between adjacent second lines and extend in a second direction that is traverse to the first direction. Additionally, the distance between adjacent first lines of the first grid is different than the distance between adjacent first lines of the second grid, and the distance between adjacent second lines of the first grid is different than the distance between adjacent second lines of the second grid.

BRIEF DESCRIPTION OF THE DRAWINGS

A better understanding of the exemplary embodiments may be understood by reference to the attached drawings, in which like reference numbers designate like parts. In accordance with common practice, various features of the drawings are not drawn to scale unless otherwise indicated. To the contrary, the dimensions of the various features may be expanded or reduced for clarity. The drawings are exemplary and not intended to limit the claims in any way.

DETAILED DESCRIPTION OF THE INVENTION

Aspects of the present invention are directed to fiducial marking systems and to coordinate systems formed from fiducial marking systems. The present invention is not intended to be limited to the details of the embodiments described below. Instead, various modifications may be made in the details within the scope and range of equivalents of the claims and without departing from the invention.

Figure 1:
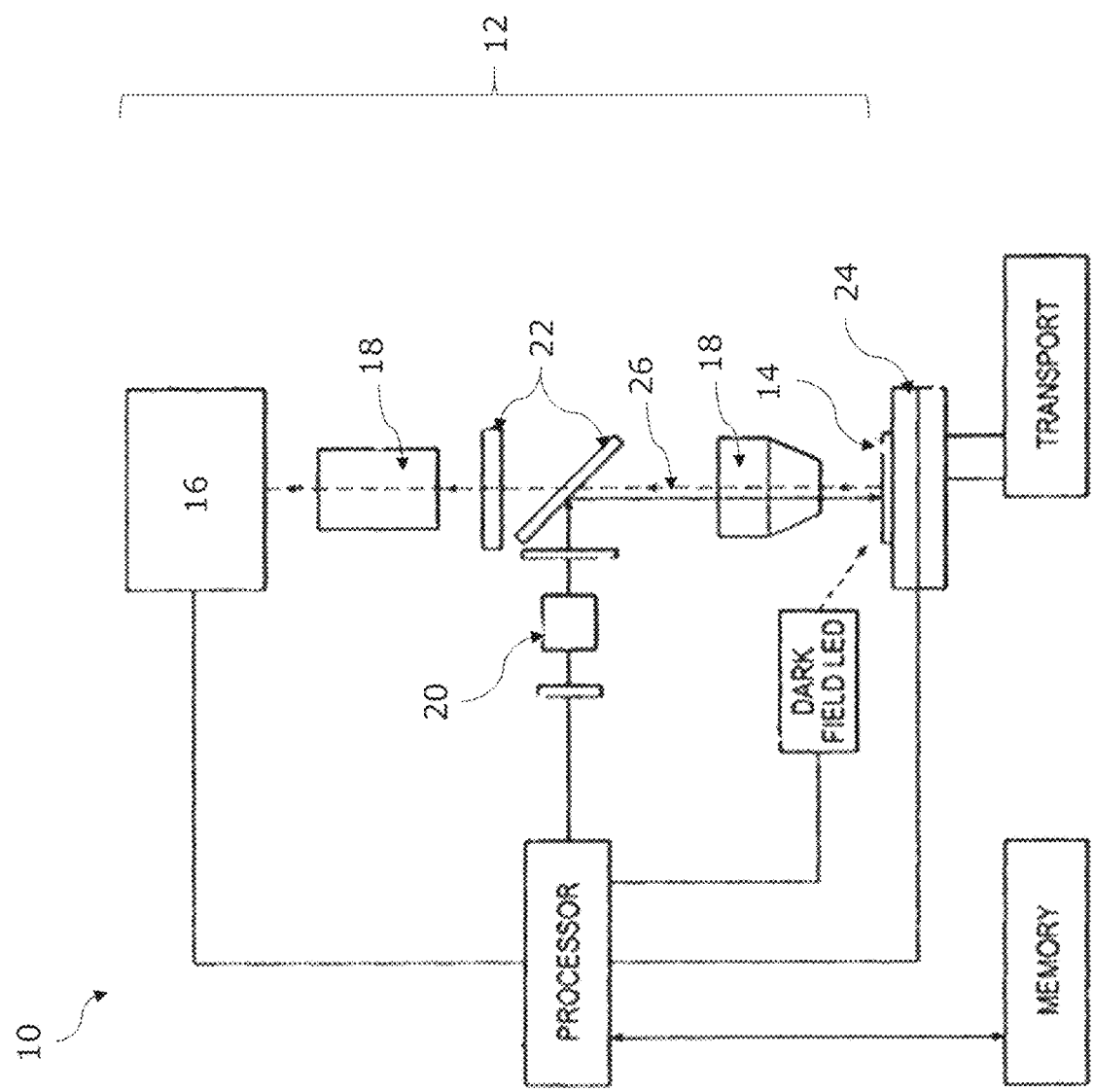
FIG. 1 depicts a system for imaging a target surface having fiducial markings in accordance with aspects of the invention.

FIG. 1 depicts an imaging system 10 for imaging a target surface 14 having fiducial markings in accordance with aspects of the invention. Imagining system 10 includes an optical system 12 that is configured to image a target surface 14 that has nucleic acids, DNA, proteins, and/or other biological materials contained thereon. The optical system 12 may include, for example, a camera 16 (e.g., a CCD or other digital camera as known in the art), one or more lenses 18 (e.g., focusing lenses, collimating lenses, etc.), one or more light sources 20 (e.g., lasers, high-intensity light emitting diodes, etc.), and one or more wavelength filters 22 (e.g., bandpass filters, dichroic mirrors, etc.). The target surface 14 may be mounted on a stage 24. The various components are controlled by a processor (e.g., a CPU or the like). One or more components of the optical system 12 and the stage 24 may be movable to position the target surface 14 in the focal plane of the camera 16, and to move laterally (i.e., perpendicular to the viewing axis 26) to allow the camera 16 to image different parts of the target surface 14. Examples of suitable imaging systems are described in U.S. Pat. No. 9,591,268 and U.S. Patent Publication no. 2017/0182493, which are both incorporated herein in their entirety for all purposes.

Figure 2:
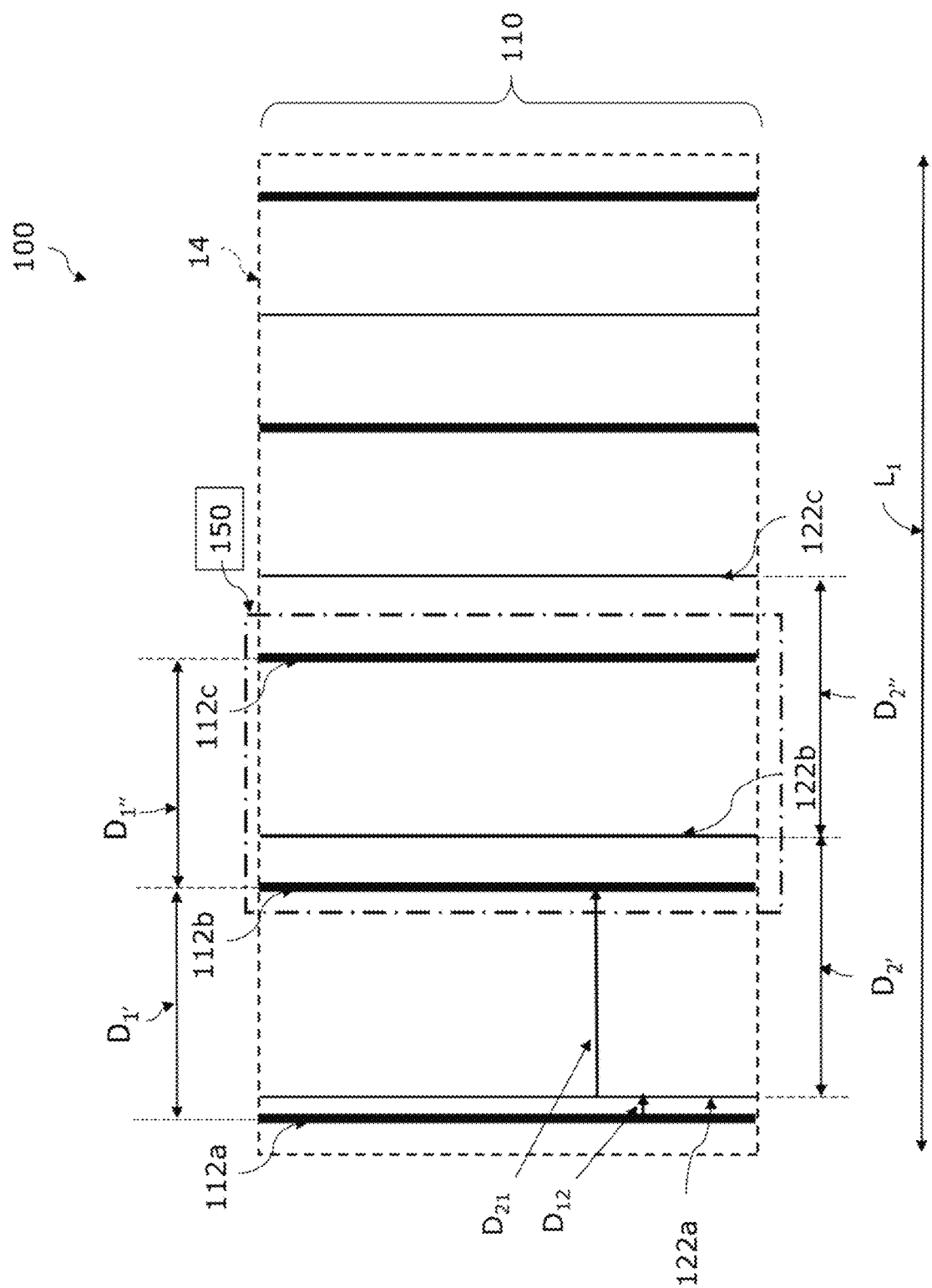
FIG. 2 depicts an embodiment of a fiducial marking system for forming a coordinate system according to aspects of the invention.
Figure 3:
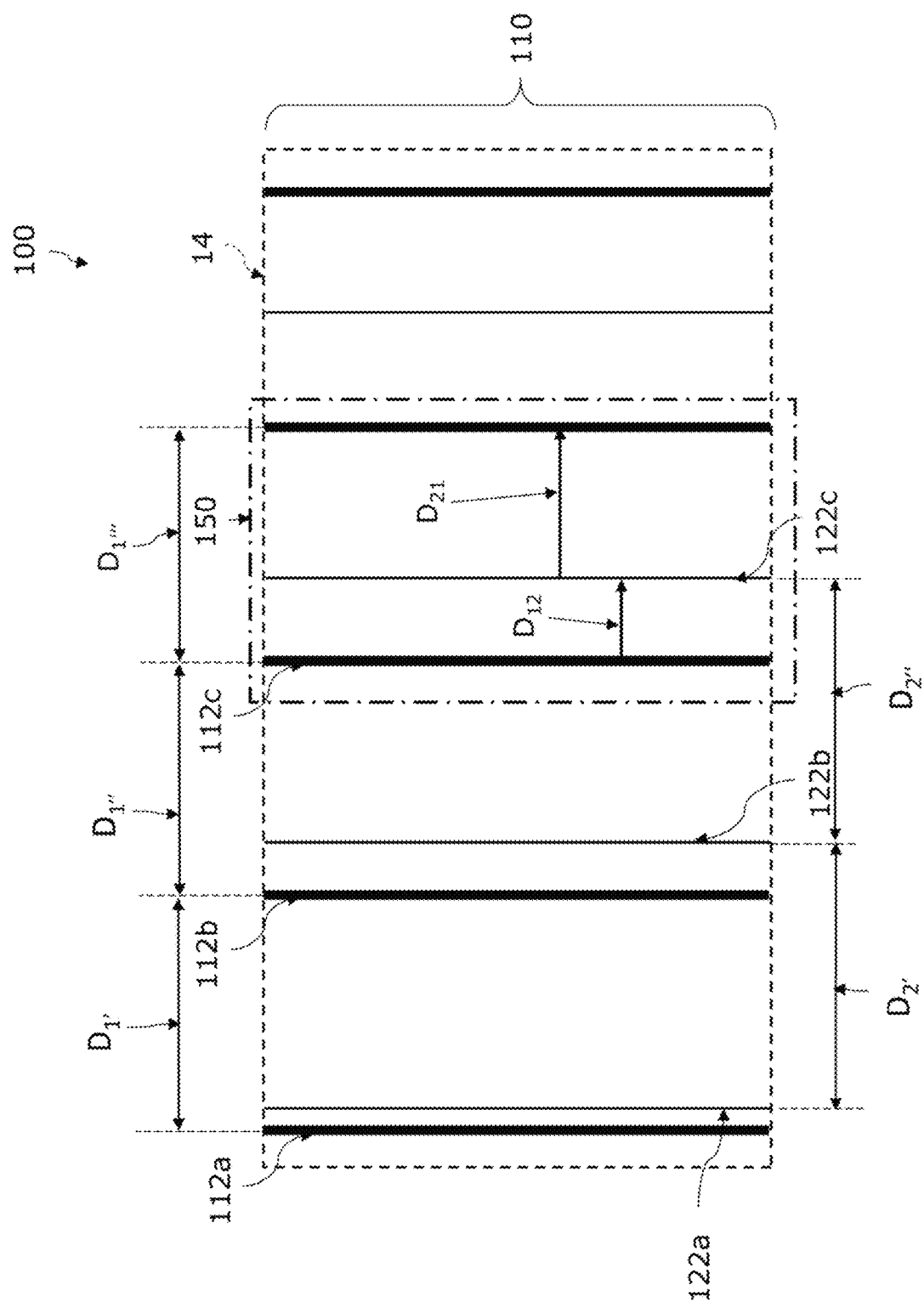
FIG. 3 depicts the fiducial marking system of FIG. 2 with a different location of the field of view relative to the target surface.

FIG. 2 depicts a first exemplary embodiment of a fiducial marking system 100 configured for forming a coordinate system that can be associated with the target surface 14 to establish a known positional relationship between the target surface 14 and the optical system 12. Fiducial marking system 100 includes a visual pattern 110 having a first plurality of lines 112 and a second plurality of lines 122. Each of the plurality of first lines 112 is spaced a distance $D_1$ from adjacent first lines 112. Adjacent first lines 112 may be spaced from each other by a first interval distance, such as first distance $D_1$. The first distance $D_1$ preferably is uniform throughout the visual pattern 110. For example, first line 112b may be spaced from first line 112a and first line 112c by the same interval of spacing, such that distance $D_{1'}$ between first line 112a and first line 112b is the same as distance $D_{1''}$ between first line 112b and first line 112c. One or more of the plurality of first lines 112 may be parallel to each other, and in preferred embodiments, all of the plurality of first lines 112 are parallel to each other. The plurality of first lines 112 also may have a common visual appearance, such that the plurality of first lines 112 are readily identifiable from the plurality of second lines 122. The defining visual appearance may be, for example, a property such as the thickness, angular orientation, coloring, dash marks, chemical labeling of the first lines 112, and/or the like.

Visual pattern 110 includes of a plurality of second lines 122 that are spaced by a second interval distance $D_2$ from adjacent second lines 122. The second distance $D_2$ between the second lines 122 preferably is uniform. For example, second line 122b may be spaced from second line 122a and second line 122c by the same interval of spacing, such that distance $D_{2'}$ between second line 122a and second line 122b is the same as distance $D_{2''}$ between second line 122b and second line 122c. The plurality of second lines 122 also may share a common visual appearance, such that the plurality of second lines 122 is readily identifiable, by e.g., visual means, such as by the thickness, angular orientation, coloring, dash marks, chemical labeling of the second lines 122, and/or the like. Preferably, the visual appearance of the plurality of second lines 122 is different from the visual appearance of the plurality of first lines 112. For example, as shown in FIG. 2 the second lines 122 may be thinner than the first lines 112.

One or more of the plurality of second lines 122 may be parallel to each other, and in a preferred embodiment all of the plurality of second lines 122 are parallel with each other.

Figure 4:
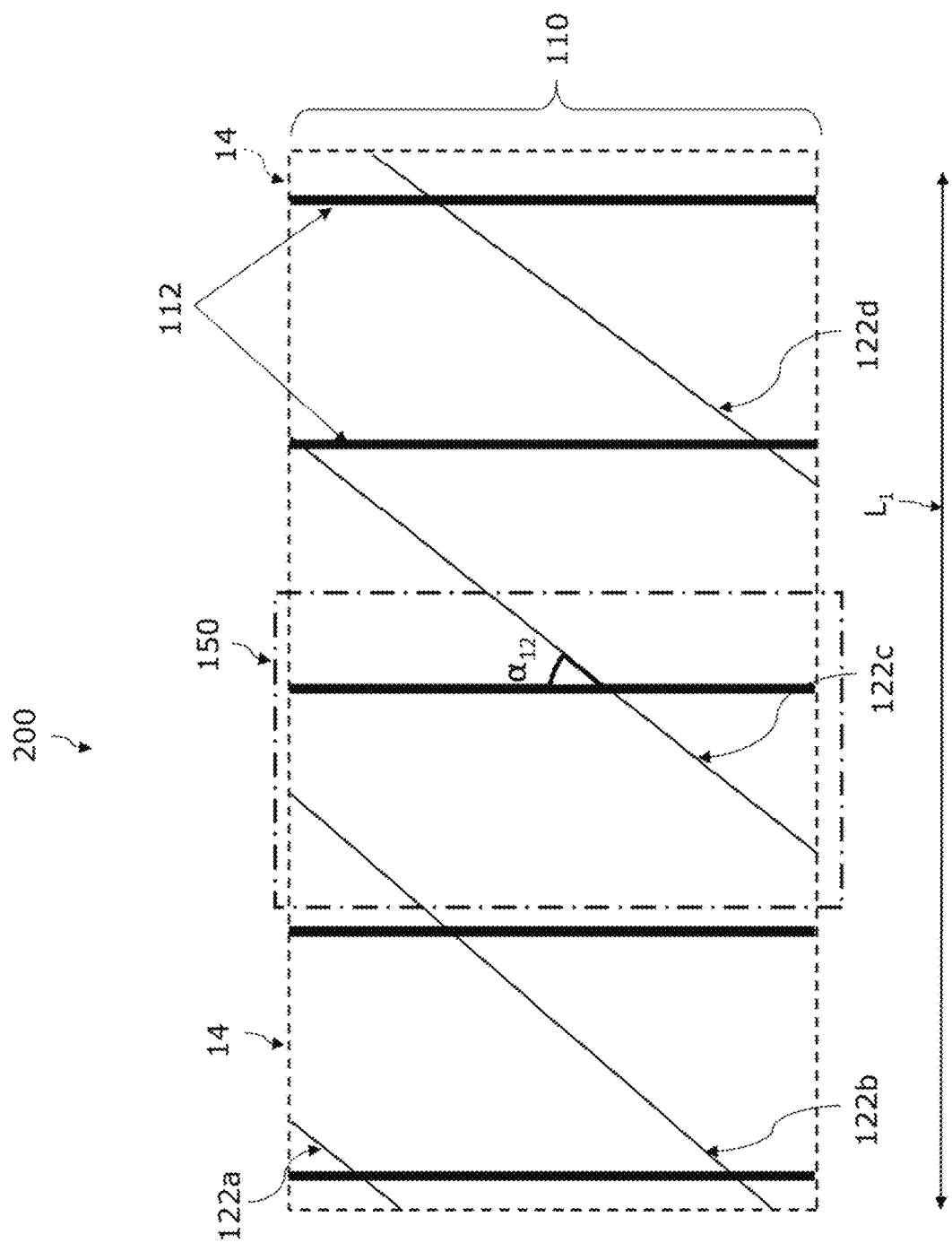
FIG. 4 depicts a further embodiment of a fiducial marking system with the plurality of second lines oriented at an angle with respect to the plurality of first lines in accordance with aspects of the invention.

The plurality of second lines 122 also may be parallel to the plurality of first lines 112. However, as illustrated in FIG. 4, the plurality of second lines 122 may be oriented at an angle $\alpha_{12}$ relative to the plurality of first lines 112. For example, the plurality of second lines 122 may be oriented relative to the plurality of first lines 112 at an angle $\alpha_{12}$ of 60° (clockwise or counterclockwise). This orientation is expected to be useful in situations in which the target surface is expected to be populated with samples that pack in a repeating pattern with the smallest unit being an equilateral triangle, such as a dense packing of generally spherical DNA template beads. In this situation, the plurality of first lines 112 may be oriented along one axis in which they do not intercept any of the samples, and the plurality of second lines 122 can be oriented along another axis in which they do not intercept any of the samples. Other orientations may be used as desired, or as may be useful to address different sample packing configurations.

Referring back to FIG. 2, the first distance D1 and second distance D2 preferably are selected to provide a unique gap distance between each individual second line 122 and the two immediately adjacent first lines 112. To this end, the plurality of second lines 122 may be positioned with respect to the plurality of first lines 112 to have a single second line 122 positioned between each adjacent pair of first lines 112. This may be accomplished, for example, by making first distance $D_1$ less than second distance $D_2$.

In this embodiment, there is a first gap $D_{12}$ between each first line 112 and the immediately adjacent second line 122 to the right and a second gap $D_{21}$ between that second line 122 and the next adjacent first line 112 to the right. Across the entirety of the visual pattern, each first gap $D_{12}$ may be different from each other first gap $D_{12}$, and each second gap $D_{21}$ may be different from each other second gap $D_{21}$.

Using this system, any first gap $D_{12}$ or second gap $D_{21}$ that is visible within the field of view 150 of the camera 16 can be measured to determine its unique value, and this value can be used to determine precisely where the field of view 150 is positioned within the visual pattern 110. For example, the field of view 150 may be known to span a predetermined number of pixel units, the locations of each first line 112 and each second line 122 on the target surface 14 may be known, and each individual value of the first gap D12 and the second gap D21 may be stored in the processor memory as a function of pixel units with the camera 16 focused at the correct focal distance from the target surface 14. As the camera 16 moves relative to the target surface 14, each gap $D_{12}$, $D_{21}$ comes into the field of view 150, and the size of the gap $D_{12}$, $D_{21}$ can be measured in pixel units to determine which particular gap $D_{12}$, $D_{21}$ is within the field of view. Once a particular gap $D_{12}$, $D_{21}$ is identified by measuring its size, the processor can identify which particular first line 112 and second line 122 are within the field of view 150, and thus can determine precisely where the field of view 150 is located based on the known locations of each individual first line 112 and second line 122.

The first distance $D_1$ and the second distance $D_2$ preferably are selected such that at least one first line 112 and at least one second line are within the field of view 150 of the camera 16 at all relative positions of visual system 10 and target surface 14. This ensures that the location of field of view 150 may be identified at all relative positions of visual system 10 and target surface 14, at least with respect to the direction $L_1$ of the spacing between second lines 122 and first lines 112.

Figure 5:
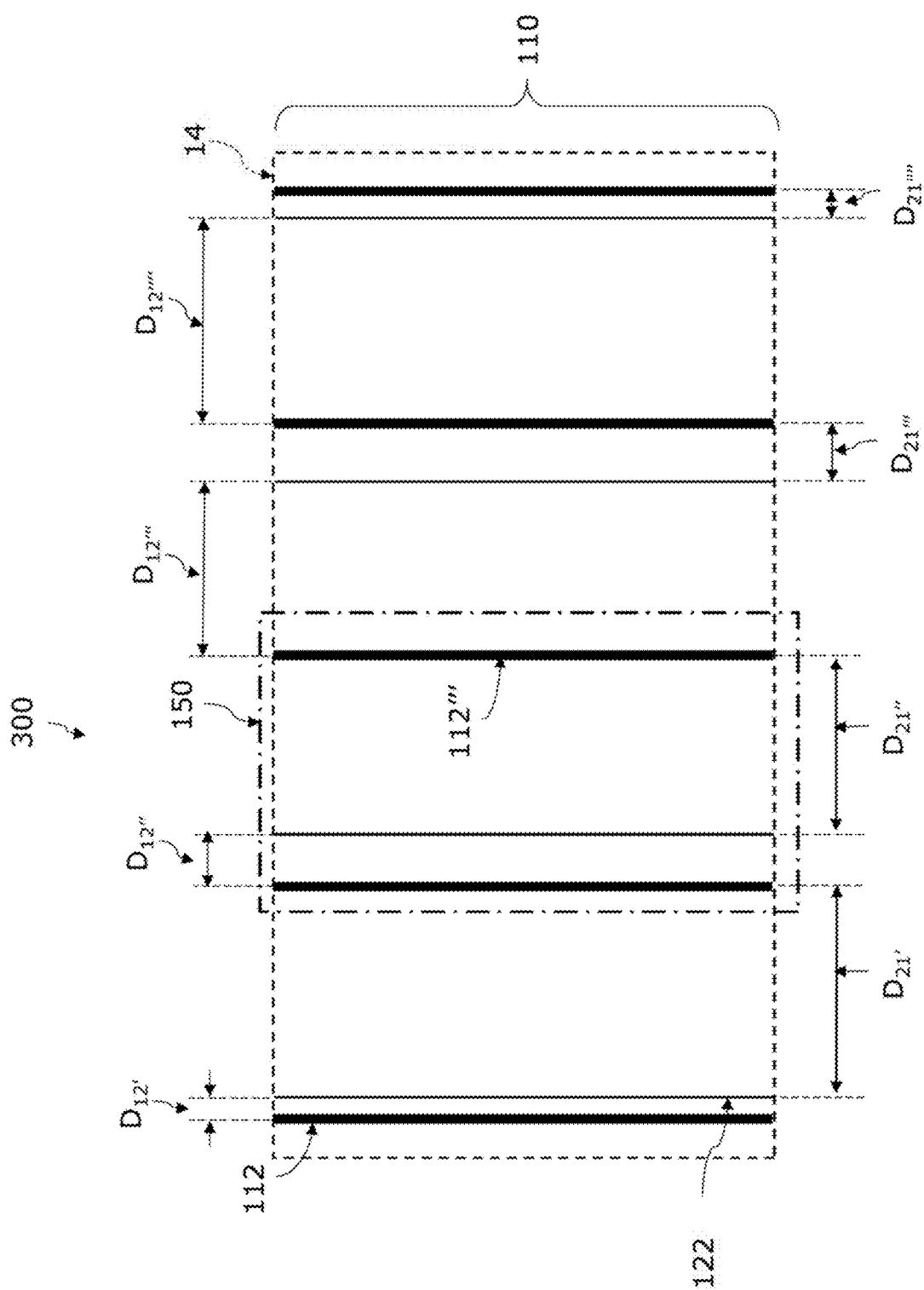
FIG. 5 depicts another embodiment of a fiducial marking system for forming a coordinate system according to aspects of the invention.

Referring now to FIG. 5, a fiducial marking system 300 may have a visual pattern 110 that includes repeating gap distance values. In this case, one gap distance $D_{12}$, $D_{21}$ between first lines 112 and second lines 122 is not unique from each other gap distance $D_{12}$ or $D_{21}$. In the embodiment of FIG. 5, the first distance $D_1$ and second distance $D_2$ are sized such that the visual pattern 110 forms a mirror image with a line of symmetry oriented along the third first line 112''' (in this case, the first distance $D_1$ is uniform, but the second distance $D_2$ varies across the line of symmetry). This results in certain first gaps $D_{12}$ being equal to certain second gaps $D_{21}$. For example, first gap $D_{12'}$ is equal in size to second gap $D_{21''''}$. Although the first gaps $D_{12}$ and second gaps $D_{21}$ are not all unique in the embodiment of FIG. 5, the visual pattern 110 still provides a coordinate system suitable for uniquely identifying the location of the field of view 150 at all possible locations. This can still be accomplished by differentiating between gaps with the same size based on the relative positions of the first line 112 and the second line 122. For example, first gap $D_{12'}$ is distinguishable from second gap $D_{12''''}$ by the relative positions of the first line 112 and second line 122. Thus, the gap distances are not unique, but other properties of each gap are unique.

As noted above, the foregoing embodiments provide a fiducial marking system that is sufficient to identify the exact location of the field of view 150 relative to the target surface 14 with respect to the direction of the spacing between the first lines 112 and the second lines 122. Other embodiments also provide the ability to uniquely identify the position of the field of view 150 in additional directions. An example of such an embodiment is illustrated in FIG. 6.

Figure 6:
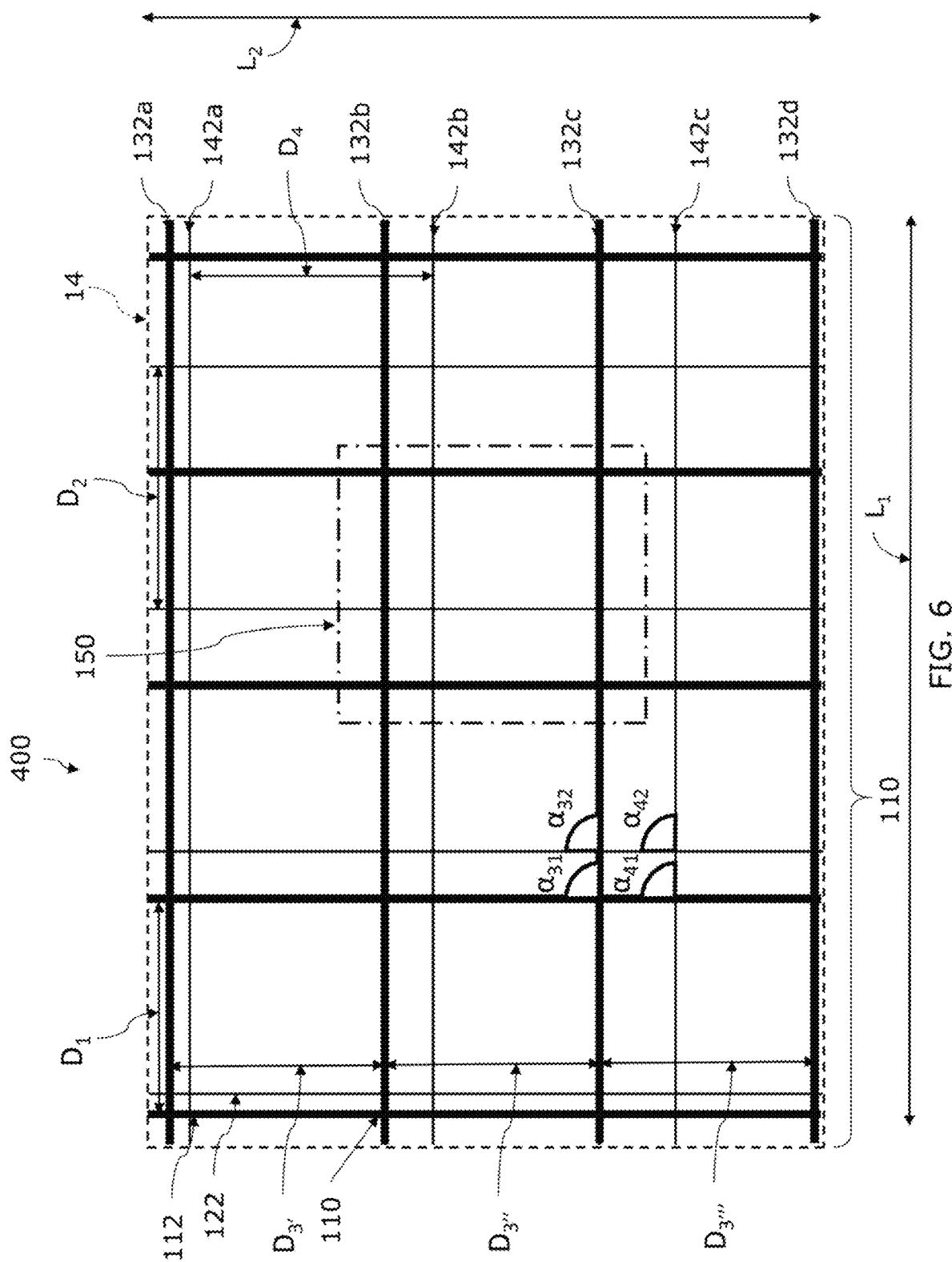
FIG. 6 depicts an embodiment of a fiducial marking system having a visual pattern formed by a first grid and a second grid according to aspects of the invention.

FIG. 6 depicts another embodiment of a fiducial marking system 400. Fiducial marking system 400 includes features that are similar to the features of fiducial marking systems 100, 200 and 300; thus, similar reference numbers and nomenclatures are used to refer to similar features. Additionally, for brevity, discussions of one or more features of fiducial marking system 400 may be omitted if such features are disclosed with reference to other embodiments of the invention.

Fiducial marking system 400 includes a visual pattern 110 comprising a plurality of first lines 112, a plurality of second lines 122, such as discussed above, and also includes a plurality of third lines 132, and a plurality of fourth lines 142. Each of the plurality of third lines 132 is spaced by distance $D_3$ from adjacent third lines 132. Adjacent third lines 132 may be spaced from each other by an interval, such that distances $D_{3'}$, $D_{3''}$ and $D_{3'''}$ between third lines 132a-132d are equal or substantially similar. One or more of the plurality of third lines 132 may be parallel to each other and, in a preferred embodiment, each of the plurality of third lines 132 is parallel to the others. The plurality of third lines 132 may have a common visual appearance, such that each of the plurality of third lines 132 is readily identifiable, e.g., by visual means, such as the thickness, orientation, coloring, dash marks, chemical labeling of third lines 132, and/or the like.

Visual pattern 110 also includes of a plurality of fourth lines 142 that are spaced by a distance $D_4$ from adjacent fourth lines 142. Each fourth line 142 may be spaced from adjacent fourth lines 142 by an interval, such that the distance $D_4$ between fourth lines 142 is equal or substantially similar. One or more of the plurality of fourth lines 142 may be parallel to each other, and in a preferred embodiment, all of the plurality of fourth lines 142 is parallel to each other. That plurality of fourth lines 142 may be oriented in a direction that is parallel to the orientation of the direction of plurality of third lines 132. The plurality of fourth lines 142 may have a common visual appearance, such that each of the plurality of fourth lines 142 is readily identifiable, e.g., by visual means, such as the thickness, orientation, coloring, dash marks, chemical labeling of fourth lines 142, and/or the like.

Preferably, the visual appearance and/or the orientation of each of plurality of first lines 112, plurality of second lines 122, plurality of third lines 132, and plurality of fourth lines 142 is different, such that each of the plurality of lines 112, 122, 132, and 142 may be readily identifiable and/or distinguishable. In the embodiment illustrated in FIG. 6, the plurality of third lines 132 has a thickness that is different from the thickness of the plurality of fourth lines 142, which provides the plurality of third lines 132 a visual appearance that is different form the visual appearance of the plurality of fourth lines 142. Additionally, in the embodiment of FIG. 6, each of the plurality of first lines 112 is parallel to each of the plurality of second lines 122 and each of the plurality of third lines 132 is parallel to each of the plurality of fourth lines 142.

The plurality of third lines 132 and/or the plurality of fourth lines 142 may be configured to traverse the plurality of first lines 112 and/or the plurality of second lines 122. For example, the plurality of first lines 112 may be oriented in a first direction, the plurality of second lines 122 may be oriented in a second direction, the plurality of third lines 132 may be in oriented in a third direction and the plurality of fourth lines 142 may be oriented in a fourth direction, and one or both of the third and fourth directions may be non-parallel with one or both of the first and second directions to cause the respective pluralities of lines to periodically intersect one another. In one embodiment, the first direction is parallel to the second direction, and the third direction is parallel to the fourth direction, and the third and fourth directions are angled relative to the first and second directions (e.g., angled at 90 degrees or 60 degrees). Visual pattern 110 also may be configured such that the first lines 112 and third lines 132 form a first rectilinear grid with all of its lines having a first thickness, and the second lines 122 and fourth lines 142 form a second rectilinear grid with all of its line having a second thickness that is different from the first thickness. Also, distance $D_1$ may be equal or substantially similar to distance $D_3$ and distance $D_2$ may be equal or substantially similar to distance $D_4$, such that the rectilinear grid formed by the first lines 112 and third lines 132 is a first pattern of squares, and the rectilinear grid formed by the second lines 122 and fourth lines 142 is a second pattern of squares. Other alternatives and variations will be apparent to persons of ordinary skill in the art in view of the present disclosure.

Although the third lines 132 and the fourth lines 142 are illustrated in FIG. 6 as traversing the first lines 112 and the second lines 122 at a perpendicular angle, the third lines 132 and/or fourth lines 142 may be oriented at any angle that would traverse the first lines 112 and/or second lines 122. For example, the third lines 132 and/or fourth lines 142 may be oriented with respect to the first lines 112 and/or second lines 122 at an angle $\alpha_{31}$, $\alpha_{32}$, $\alpha_{41}$, and/or $\alpha_{42}$ of 60° or at other angles that might be found to be useful with routine experimentation based on the present disclosure. It is also envisioned that additional lines may be added to the visual pattern 110.

The fourth lines 142 may be positioned with respect to the third lines 132 to have a single fourth line 142 positioned between an adjacent pair of third lines 132. In one embodiment, no more than one of the fourth lines 142 is positioned between each adjacent pair of third lines 132. The visual pattern 110 preferably is configured to have a fourth distance $D_4$ between each adjacent pair of fourth lines 142 that is different from the third distance $D_3$ between each adjacent pair of third lines, such that each fourth line 142 is positioned relative to adjacent third line(s) 132 in a position that is unique and/or different from the position of each other fourth line 142 relative to its respective adjacent third line(s) 132.

For example, the visual pattern 110 may be configured such that gap $D_{34}$ and/or $D_{43}$ between each unique fourth line 142 and its adjacent third line or lines 132 is different from the gap $D_{34}$ and/or gap $D_{43}$ between each other fourth line 142 relative to its respective adjacent third lines 132. Thus, as explained above in relation to the embodiments above, the gap values may be used to identify which particular third line 132 and fourth line 142 are observed at any given position along the direction of in which the gaps extend $L_2$.

The first distance $D_1$, second distance $D_2$, third distance $D_3$, and fourth distance $D_4$ preferably are selected such that at least one first line 112, at least one second line 122, at least one first line 132, and at least one fourth line 142 are within field of view 150 at all relative positions of visual system 10 and target surface 14. Thus, the visual pattern 110 may form a global coordinate system, whereby the unique positioning of each of the plurality of second lines 122 relative to adjacent first lines 112 and the unique positioning of each of the plurality of fourth lines 142 relative to adjacent third lines 132 enables the determination of the location of field of view 150.

For example, visual pattern 110 may form a coordinate system in the direction of the distance (e.g., in the direction of $L_2$ in FIG. 6) between the fourth lines 142 and the third lines 132 by configuring each of the fourth lines 142 to have a unique position relative to adjacent third line(s) 132. As discussed with reference to fiducial marking system 100, visual pattern 110 may be configured such that each of the second lines 122 has a unique position relative to adjacent first line(s) 112 that produces a coordinate system in the direction of the distance (e.g., in the direction of $L_1$ in FIGS. 2 and 6) between the second lines 122 and first lines 112. By configuring visual pattern 110 to form a coordinate system in at least two directions (e.g., in the direction of $L_1$ and $L_2$ in FIG. 6), visual pattern 110 may form a global coordinate system that enables identification of the location of field of view 150 at all relative positions of visual system 10 and target surface 14.

Although fiducial marking system 400, as illustrated in FIG. 6, is configured to form a Cartesian coordinate systems, embodiment of the invention may be configured to form other types of coordinate systems, such as polar coordinate system.

Figure 7:
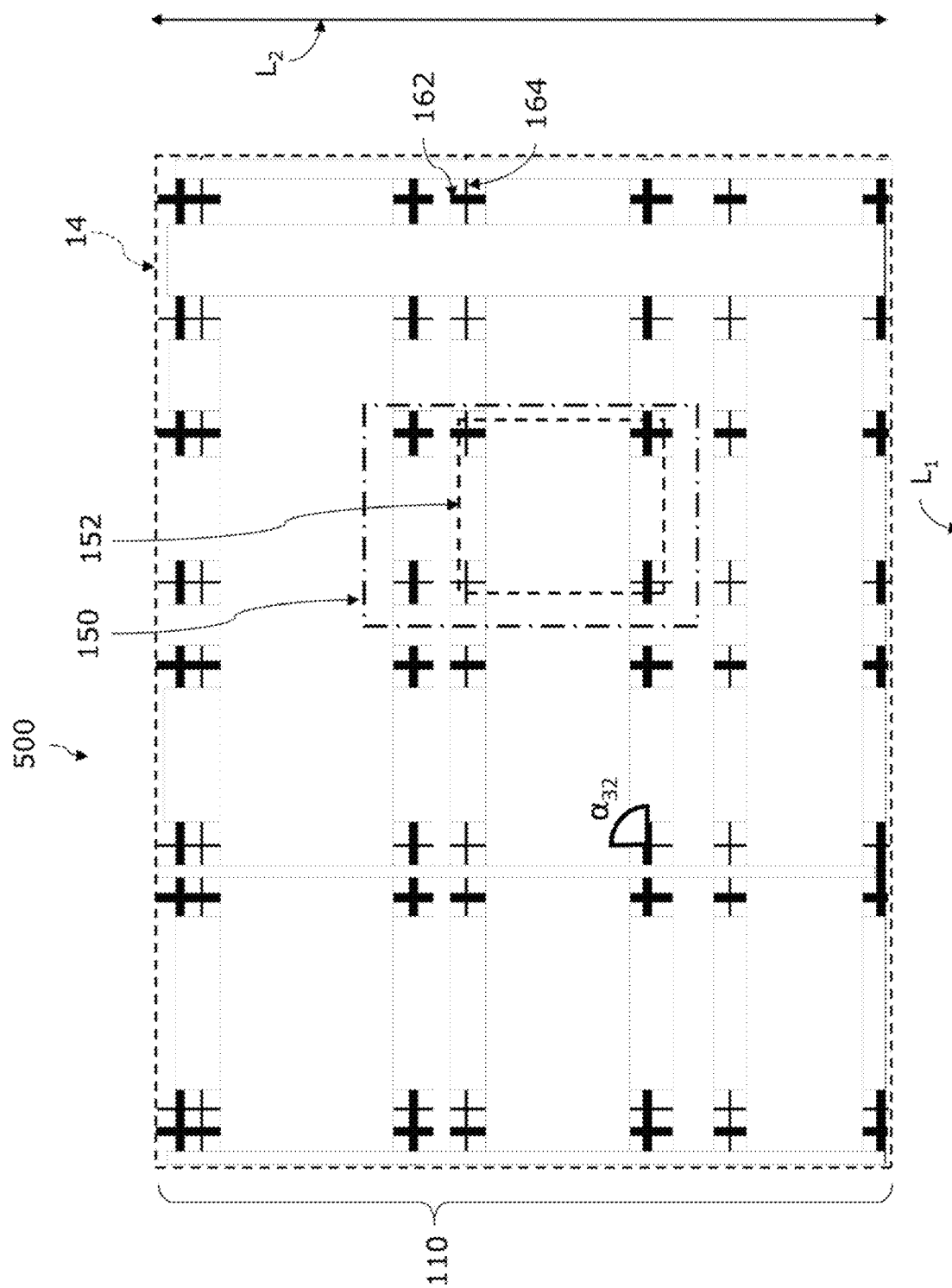
FIG. 7 depicts an embodiment of a fiducial marking system having a visual pattern formed from crosshairs in accordance with aspects of the invention.

FIG. 7 depicts an embodiment of a fiducial marking system 500 having a visual pattern 110 comprising crosshairs 160. Fiducial marking system 500 includes features that are similar to the features of fiducial marking systems 100-400 and, thus, similar reference number may be used to refer to similar features.

Each crosshair 160 include a first intersector 162 extending in a respective direction $L_2$, and a second intersector 164 extending in a respective direction $L_1$ and intersecting the first intersector 162 to form crosshair 160. First intersector 162 and second intersector 164 may be formed from a plurality of lines, such as plurality of first lines 112, plurality of second lines 122, plurality of third lines 132, and/or plurality of lines 142. For example, first intersector 162 and second intersector 164 may be formed by orienting a plurality of third lines 132 and a plurality of fourth lines 142 to traverse a plurality of first lines 112 and a plurality of second lines 122, such as discussed above in relation to FIG. 6, but where sections of the plurality of lines 112, 122, 132, and 142 between the intersections are removed to produce the shapes of crosshairs 160.

In one embodiment, each first intersector 162 formed from second lines 122 has position relative to adjacent first intersectors 162 formed from first lines 112 that is unique or different from other first intersectors 162 formed from second lines 122 relative their adjacent first intersectors 162 formed from first lines 112. Additionally and/or alternatively, each second intersector 164 formed from fourth lines 142 has a position relative to adjacent second intersectors 164 formed from third lines 132 that is unique or different from other second intersectors 164 formed from fourth lines 142 relative their adjacent second intersectors 164 formed from third lines 132.

Visual pattern 110 may be configured such that at least a majority of four crosshairs 160 are within field of view 150 at all relative positions of visual system 10 and target surface 14. It is not strictly necessary for the entire crosshair to be visible to be able to use it's intersection point as a fiducial marker. For example, as indicated by field of view 152 in FIG. 7, a fiducial measurement can be established even if only a portion of each of four crosshairs is within the field of view 152. Thus, by configuring crosshairs 160 to be formed from first intersectors 162 and second intersectors 164 having visual appearances and unique positions similar to the plurality of lines 112, 122, 132, and/or 142, visual pattern 110 may be configured to form a coordinate system whereby the location of field of view 150 may be determined from at least a majority of four crosshairs 160.

Figure 8:
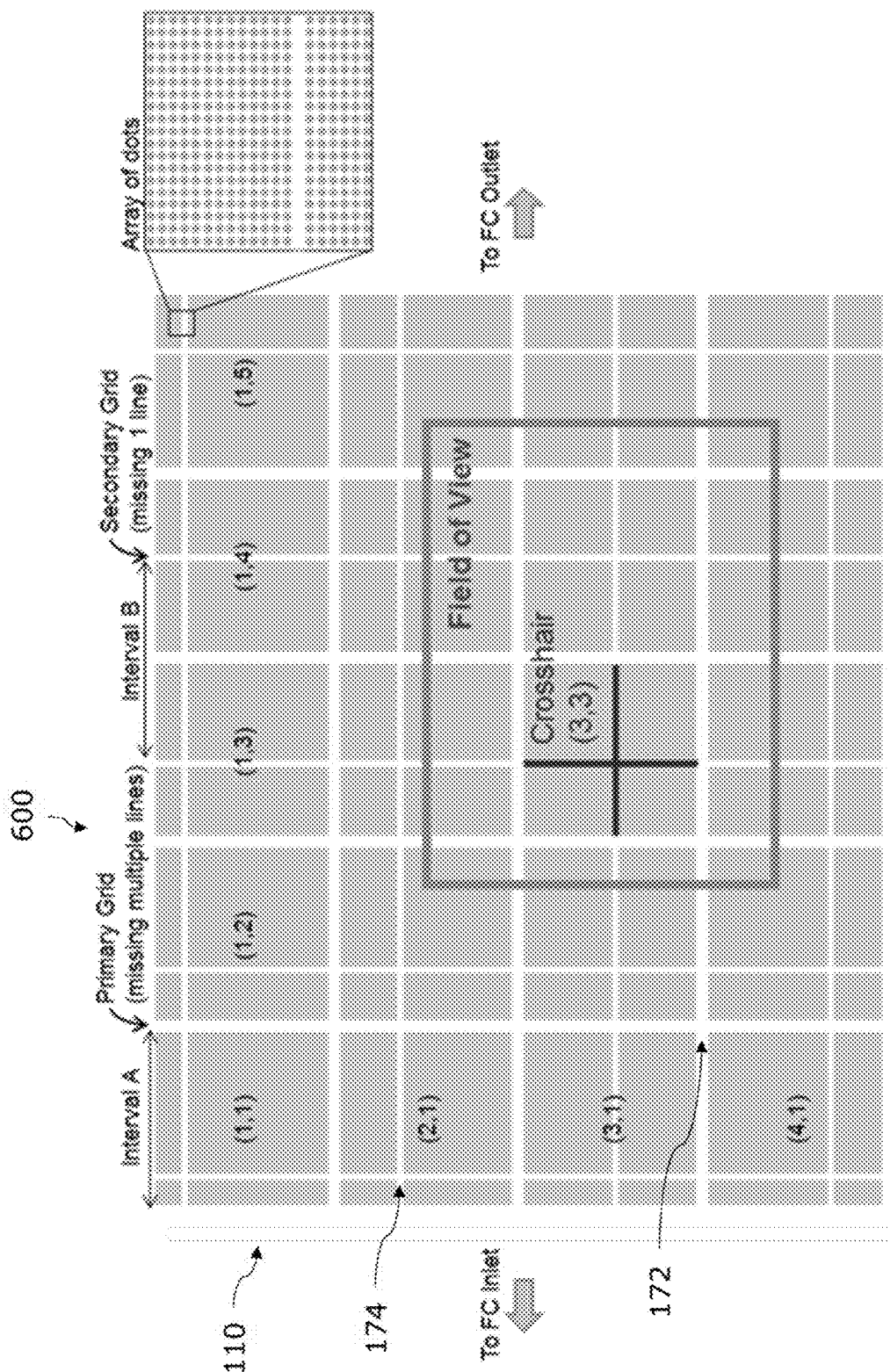
FIGS. 8 and 9 depict additional embodiments of fiducial marking systems having a visual pattern forming at least two grids according to aspects of the invention.
Figure 9:
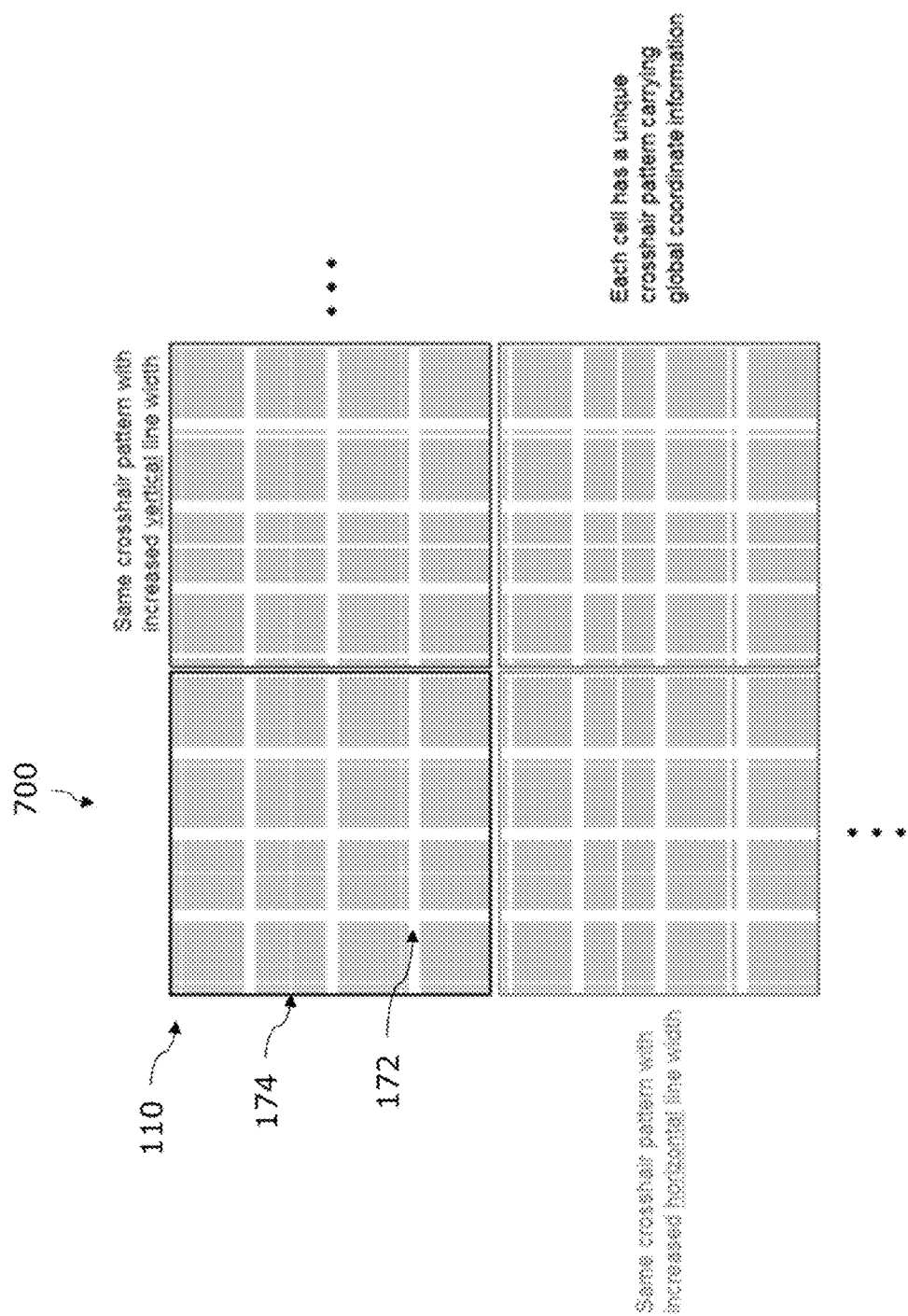

FIGS. 8 and 9 depict additional embodiments of fiducial marking systems according to aspects of the invention. Fiducial marking systems 600 and 700 include features that are similar to the features of fiducial marking systems 100-500 and, thus, similar reference number may be used to refer to similar features. Additionally, discussions of one or more features of fiducial marking systems 600 and 700 are omitted when such features are disclosed with reference to other embodiments of the invention.

Fiducial marking systems 600 and 700 include a visual pattern 110 formed from a first grid 172 and a second grid 174. First grid 172 is formed from a plurality of first lines 112 and by a plurality of third lines 132. The first lines 112 extend in a first direction $L_1$ and have a distance $D_1$ between adjacent first lines 112. The third lines 132 extend in a second direction $L_2$ that is traverse to the first direction $L_1$ and have a distance $D_3$ between adjacent third lines 132.

Second grid 174 is formed by a plurality of second lines 122 and by a plurality of fourth lines 142. The second lines 122 extend in first direction $L_1$ and have a distance $D_2$ between adjacent second lines 122. The fourth lines 142 extend in a second direction $L_2$ that is traverse to first direction $L_1$ and have a distance $D_4$ between adjacent fourth lines 142. Distance $D_1$ between adjacent first lines 112 of first grid 172 is different than distance $D_2$ between adjacent second lines 122 of the second grid 174, and distance $D_3$ between adjacent third lines 132 of the first grid 172 is different than the distance $D_4$ between adjacent fourth lines 142 of second grid 174.

The embodiment of FIG. 8 illustrates a full-size crosshair formed by continuous lines forming the first grid 172. Each crosshair has a unique configuration of line distances extending from the intersection point to the adjacent line of the second grid 172. FIG. 8 also illustrates how the lines are formed as gaps in an array of "dots" formed by the locations of DNA template bead locations.

The embodiment of FIG. 9 illustrates one technique for addressing visual patterns 700 in which the spacing between first, second, third and fourth lines repeats. In this example, the first, second, third and fourth distances (i.e., the distances between adjacent, first, second, third and fourth lines, respectively) are selected such that the pattern of gap sizes (i.e., the crosshair size pattern) is not unique at each location on the visual pattern. Rather, each quadrant has the same pattern of gap distances as each other quadrant. To account for this, the pattern 700 uses different visual indicators to distinguish each quadrant from the others. In this case, the line thickness of one or more lines forming the pattern varies in each quadrant. Thus, even though the gap distance between line centers at a particular location on one quadrant may be equal to the gap distance between similar line centers at a different quadrant, the properties of the lines are selected to allow unique positional determination.

The visual patterns described herein can be a associated with at least a portion of the target surface using any suitable technique. For example, the visual pattern may be printed or etched (e.g., using photolithography methods or the like) on a portion of a sequencing chip comprising a metallic backing plate with a transparent cover that form a flowcell channel therein. In one exemplary embodiment, the visual pattern is coplanar with a target surface upon which the DNA template spots are immobilized, but this is not strictly required. For example, in other cases, the visual pattern may be printed on an outer surface of a transparent (e.g., glass) plate, and the target surface may be an inner surface of the transparent plate upon which the DNA template spots are immobilized. In another embodiment, the visual pattern may be formed by voids on the target surface where no DNA template spots are present. For example, the target surface may be treated with a pattern of chemical agents to selectively functionalize certain regions to immobilize DNA template spots in those regions, and the visual pattern may be created by not treating other portions of the surface so that DNA template beads are not immobilized on those portions. Then, once the target surface is populated with DNA template spots, the regions of the surface that lack DNA template spots form the visual pattern. Examples of technologies for creating a functionalized target surface on a sequencing chip are found in PCT Patent Publication No. WO 2013/184796, which is incorporated herein by reference.

Although the invention is illustrated and described herein with reference to specific embodiments, the invention is not intended to be limited to the details shown. Rather, various modifications may be made in the details within the scope and range of equivalents of the claims and without departing from the invention. Numerous variations, changes and substitutions will occur to those skilled in the art without departing from the spirit of the invention. Accordingly, it is intended that the appended claims cover all such variations as fall within the spirit and scope of the invention.

We claim:

1. A fiducial marking system for forming a coordinate system for a visual system having a limited field of view, the fiducial marking system comprising:
    a target surface that is movable relative to the visual system;
    a visual pattern associated with the target surface, the visual pattern comprising:
    a first group of parallel lines, each line in the first group spaced by a first distance from each adjacent line in the first group, and
    a second group of parallel lines, each line in the second group spaced by a second distance from each adjacent line in the second group,
    wherein the first distance is different than the second distance;
    wherein the first distance and the second distance are selected such that at least one line in the first group and at least one line in the second group are within the field of view at all relative positions of the visual system and the target surface;
    wherein all of the lines of the first group extend in a first direction, all of the lines of the second group extend in a second direction, and the first direction is parallel to the second direction;
    wherein no more than one line in the second group is positioned between each adjacent pair of lines in the first group; and
    wherein each line in the second group is positioned relative to a respective adjacent pair of lines in the first group in a position that is different from the position of each other line in the second group relative to its respective adjacent pair of lines in the first group.

2. The fiducial marking system of claim 1, wherein the lines in the first group each have a first defining visual appearance and the lines in the second group each have a second defining visual appearance, and the second defining visual appearance is different from the first defining visual appearance.

3. The fiducial marking system of claim 2, wherein the first defining visual appearance comprises a first thickness, and the second defining visual appearance comprises a second thickness, the second thickness being different from the first thickness.

4. The fiducial marking system of claim 1, wherein the visual pattern further comprises:
    a third group of lines, each line in the third group spaced by a third distance from each adjacent line in the third group; and
    a fourth group of lines, each line in the fourth group spaced by a fourth distance from each adjacent line in the fourth group;
    wherein the third distance is different than the fourth distance; and
    wherein the third distance and the fourth distance are selected such that at least one line in the third group and at least one line in the fourth group are within the field of view at all relative positions of the visual system and the target surface.

5. The fiducial marking system of claim 4, wherein:
    all of the lines in the third group extend in a third direction, the third direction being different than the first direction; and
    all of the lines in the fourth group extend in a fourth direction, the fourth direction being different than the second direction.

6. The fiducial marking system of claim 5, wherein the third direction is parallel with the fourth direction.

7. The fiducial marking system of claim 6, wherein the second direction is perpendicular with the first direction, and the fourth direction is perpendicular with the second direction.

8. The fiducial marking system of claim 6, wherein the second direction is oriented at 60 degrees to the first direction, and the fourth direction is oriented at 60 degrees to the second direction.

9. The fiducial marking system of claim 4, wherein the lines in the first group and the lines in the third group have a first defining visual appearance and the lines in the second group and the lines in the fourth group have a second defining visual appearance, and the second defining visual appearance is different from the first defining visual appearance.

10. The fiducial marking system of claim 9, wherein the first defining visual appearance comprises a first thickness, and the second defining visual appearance comprises a second thickness, the second thickness being different from the first thickness.

11. The fiducial marking system of claim 4 wherein:
    the lines in the first group intersect the lines in the third group to form a pattern of first crosshair marks;
    the lines in the second group intersect the lines in the fourth group to form a pattern of second crosshair marks; and
    each of the first crosshair marks and each of the second crosshair marks identifies a unique coordinate location on the target surface.

12. The fiducial marking system of claim 11, wherein the lines in the first group, the lines in the second group, the lines in the third group and the lines in the fourth group comprise broken lines having a gap between each intersection with each other line, such that each first crosshair mark and each second crosshair mark is separate from each other first crosshair mark and each other second crosshair mark.

13. The fiducial marking system of claim 11, wherein the lines in the first group, the lines in the second group, the lines in the third group and the lines in the fourth group comprise continuous lines, such that each first crosshair mark and each second crosshair mark is connected to each adjacent first crosshair mark and each adjacent second crosshair mark to form a continuous grid pattern on the target surface.

14. A fiducial marking system for forming a global coordinate system, the fiducial marking system comprising:
    a first grid formed by a first group of lines and by a second group of lines, the lines in the first group extending in a first direction and having a first distance between adjacent lines in the first group, the plurality of lines in the second group extending in a second direction that is transverse to the first direction and having a second distance between adjacent lines in the second group, a second grid formed by a third group of lines and by a fourth group of lines, the lines in the third group extending in the first direction and having a third distance between adjacent lines in the third group, the lines in the fourth group extending in the second direction and having a fourth distance between adjacent lines in the fourth group, wherein the first distance is different than the second distance, and the third distance is different than the fourth distance.

* * * * *